United States Patent [19]

Goldstein et al.

[11] Patent Number: 4,963,350

[45] Date of Patent: Oct. 16, 1990

[54] LIQUID SHAVING PRODUCT

[76] Inventors: Samuel A. Goldstein, Box 275, Westtown, Pa. 19395; Jose A. P. Alonso, Calle Beniajan, 57 "Los Dolores", 3001 Murcia, Murcia, Spain

[21] Appl. No.: 367,130

[22] Filed: Jun. 16, 1989

[51] Int. Cl.⁵ .............................................. A61K 7/15
[52] U.S. Cl. ...................................... 424/73; 514/828; 514/848; 514/970; 514/769; 514/772
[58] Field of Search .................. 424/73, 659; 514/390, 514/386, 828, 848, 970, 769, 772; 548/311

[56] References Cited

U.S. PATENT DOCUMENTS 4,065,422 12/1977 Lundmark et al. .................... 260/29
4,279,891 7/1981 Henkel et al. ......................... 424/73
4,416,873 11/1983 Puchalski et al. .................... 424/177

FOREIGN PATENT DOCUMENTS 156211 12/1981 Japan .................................... 514/390

Primary Examiner—Merrell C. Cashion, Jr.
Assistant Examiner—Susan S. Rucker
Attorney, Agent, or Firm—Warren F. B. Lindsley

[57] ABSTRACT

A stable soothing hydroalcoholic skin preparation for shaving purposes employing alcohol as a carrier or solvent for the remainder of the composition comprising a combined allantoin-boric acid hydrolyzed solution in combination with glycerine, menthol, ethyl alchohol and fragrance.

10 Claims, 1 Drawing Sheet

LIQUID SHAVING PRODUCT

BACKGROUND OF THE INVENTION

This invention relates to liquid products for external application to the body and more particularly to a solution or medicinal mixture for applying to circumscribed portions of the skin such as the face for shaving purposes.

Shaving soaps are usually made of a cocoanut oil as a base with some stearic acid used to give it hardness. Both soda and potash lyes are used and gum is added to prevent it from quickly drying. Glycerine is a common ingredient of this type of soap.

Transparent soaps are prepared by drying ordinary soap, dissolving it in alcohol, allowing the solution to remain at rest so long as any impurities are precipitated, decanting off the alcoholic liquid and evaporating it until it is of such a consistency as to solidify when cooled in metallic molds. Glycerine is often incoporated with transparent soaps for emollient effects, while for disinfecting purposes carbolic acid, coal tar, eucalyptus oil and other substances are added.

When such shaving soaps are used in either the solid or liquid form and removed after a shaving procedure an after shaving lotion is usually used for a cooling, stimulating, astringent, soothing or sedative effect. A good stimulating lotion is procured from a mixture of water with a third to one half of its bulk being alcohol. Astringent lotions are formed by adding from one to ten grams of sulphate of zinc or white vitriol to an ounce of very cold water having other astringents in solution. So called antiseptic lotions contain bichloride of mercury, carbolic acid or boracic acid.

A need exists for a liquid shaving product having all of the benefits of a shaving soap and the benefits of an after shaving lotion, cologne or skin toner in a single product requiring no further skin treating after a shaving activity.

The present invention relates to an alcohol based liquid shaving product which can be relatively transparent and imparts a feeling of lubricity to the product with the alcohol being a carrier or solvent for other ingredients in the composition.

DESCRIPTION OF THE PRIOR ART

Although no known liquid shaving product is known which serves as a combined shaving soap and after shaving lotion, the following patents related to personal skin products for after shaving use.

U. S. Pat. No. 4,065,422 discloses a composition which may be used on the skin or hair to impart a highly lubricated feel thereon.

U. S. Pat. No. 4,279,891 discloses a clear, aqueous, alcoholic after-shave lotion having low alcohol content.

U. S. Pat. No. 4,416,873 discloses the use of allantoin in the form of a hydroalcoholic solution, such as a cologne, after-shave lotion or skin toner containing at least about 0.5% by weight of allantoin which remains in solution without crystallizing out over an extended period of time.

SUMMARY OF THE INVENTION

In accordance with the invention claimed, a new and improved solution is provided in the form of a stable soothing hydroalcoholic skin preparation for shaving purposes.

It is, therefore, an object of this invention to provide a new and improved alcohol based personal care product which imparts a feeling of lubricity to the contacted substrate.

Another object of this invention is to provide a new and improved method of manufacture of said personal care product.

A further object of this invention is to provide an improved personal care product employing alcohol as a carrier or solvent for the remainder of the composition that serves not only as a carrier but also gives an emollient effect upon the skin and imparts a feeling of lubricity to the skin without causing crystallizing out over a period of time of any of its components.

Further objects and advantages of the invention will become apparent as the following description proceeds and the features of novelty which characterize the invention will be pointed out with particularity in the claims annexed to and forming a part of this specification.

BRIEF DESCRIPTION OF THE DRAWING

The present invention may be more readily described with reference to the accompanying drawing in which.

DESCRIPTION OF THE PREFERRED EMBODIMENT

Figure 1:
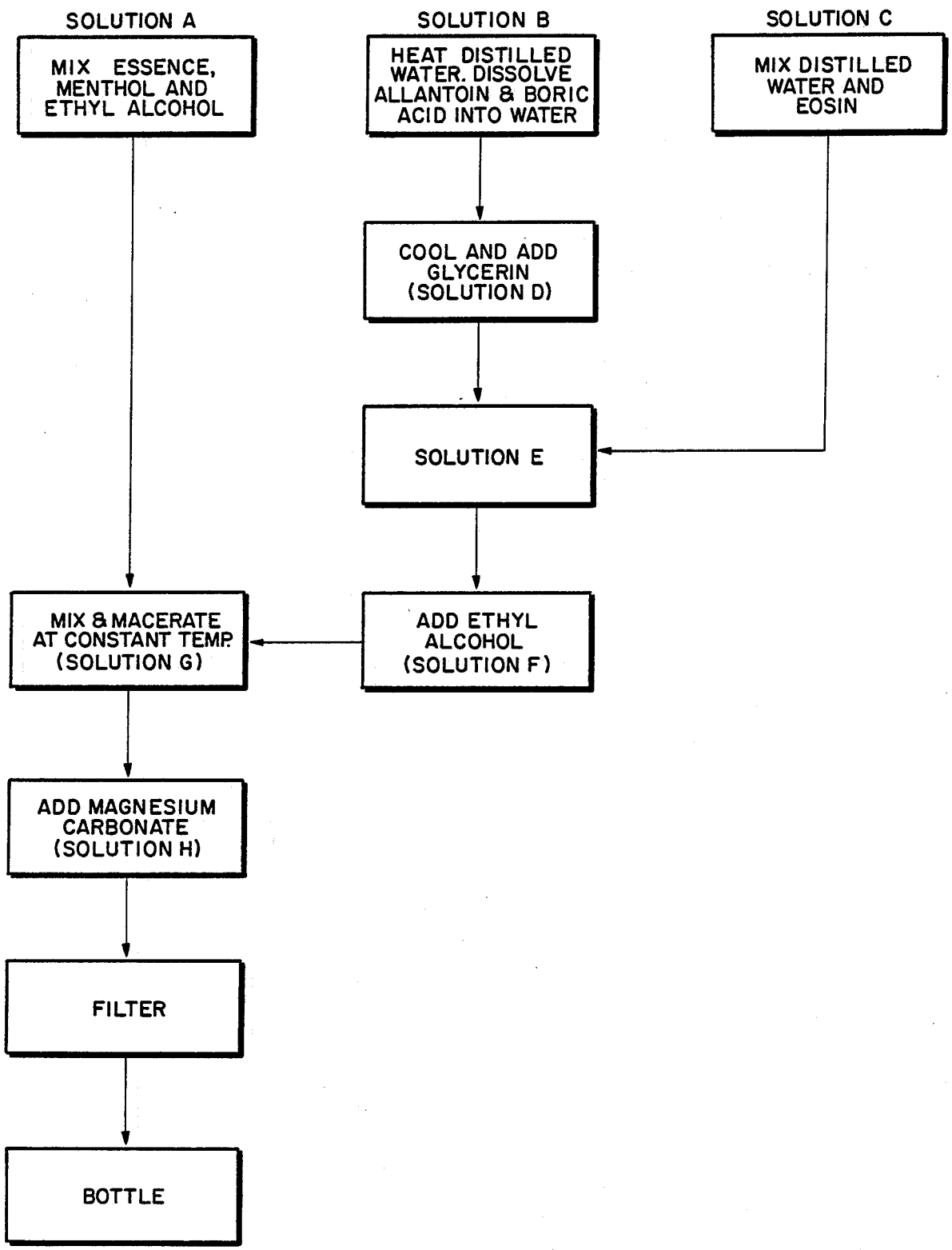
FIG. 1 of the drawing is a block diagram of the manufacturing procedure of the claimed invention.

Referring more particularly to the drawing by characters of reference, FIG. 1 discloses a block diagram of a method of manufacturing a unique and novel personal care item which may be used, for example, as a liquid shaving product with particular lubricity characteristics.

The novel product can be transparent so when used as a shaving product, the user may see the hairs on the face, legs or any other surface on the body during the shaving procedure. It not only softens the hairs, such as the beard, but also has a mild cooling, stimulating, astringent and soothing characteristic, thus obviating the need for an after shaving lotion.

The present invention is directed to an alcohol based personal care product which imparts a feeling of lubricity to the contacted skin.

Alcohol based personal care products are widely marketed with the alcohol being a carrier or solvent for the remainder of the composition and in the case of higher molecular weight alcohols such as cetyl or stearyl alcohol to not only serve as a carrier but also to give an emollient effect upon the skin, i.e., a feeling of lubricity or silkiness to the skin. In addition, alcohol is used to solubilize the perfumes, i.e., essence on fragrance used.

Further, it has been a problem when using allantoin or its derivate as a therapeutic agent to prevent it from crystallizing out of solution over a period of time.

The novel resulting product of the manufacturing process disclosed consists essentially of:

| INGREDIENTS | PARTS BY WEIGHT |
| --- | --- |
| Pure Ethyl Alcohol | 700 grams |
| Essence | 50 grams |
| Glycerine | 30 grams |
| Boric Acid | 20 grams |
| Allantoin | 2 grams |
| Menthol | 1 gram |
| H$_2$O (distilled) | 197 grams |

| INGREDIENTS | PARTS BY WEIGHT |
|---|---|
| -continued | |
| A trace of Eosin | |

To manufacture this unique product, as shown in FIG. 1 of the drawing, the following three solutions are prepared.

Solution A comprises a mixture of approximately grams of an essence with approximately 1 gram of menthol and approximately 500 cubic centimenters of pure ethyl alcohol.

Solution B comprises approximately 118 cubic centimeters of distilled water (H O) heated to approximately 70 degrees centigrade dissolving in it at this temperature approximately 2 grams of allantoin and approximately 20 grams of boric acid. Boric acid is soluble in $H_2O$ and glycerine but not in alcohol in proportions under 1/18.

Solution C comprises approximately 2,450 cubic centimeters of distilled water (H 0) in solution with approximately 1 gram of Eosin.

The ingredients identified as solution B are cooled to approximately atmospheric temperature. Then add to this 30 grams of glycerin and stir the mixture yielding a solution D.

Approximately 49 cubic centimeters of solution C are added to solution D to form a solution E.

To solution E is added approximately 230 cubic centimeters of pure ethyl alcohol (96%) to yield a solution F.

Solutions F and A are then mixed and shaked to create the final solution G which is allowed to steep (or macerate) for at least 15 days but no more than 22 days at a constant temperature of approximately 4 degrees Centigrade.

After steeping for the prescribed period of time a sufficient quantity (1 tablespoon per liter of solution) of magnesium carbonate is added to form a solution H which is filtered one or more times before the resulting liquid is bottled for use.

It should be noted that the:
Alcohol — dilates the vessels and disinfects the skin.
Essence — adds aroma i.e., fragrance to the solution.
Glycerine — is a moisturing agent in the resulting shaving product.
Boric Acid — is a disinfectant for external body use.
Allantoin — coagulates and serves as a tissue builder and healer.
Menthol — dilates vessels.
Eosin — is a coloring agent or dye $C_{20}H_8Br_4O_3$).

If so desired cetiol HE can be included as a lubricant and a nutrient for dry skin and should comprise 2% of the final solution with 15 grams of alcohol and 5 grams of $H_2O$ being removed from the formula set forth above to compensate for the addition of cetiol HE.

Solutions of triethanolamamine (50% solution) may be added in sufficient quantities to reach between 6.5 and 7.5 PH condition of the preparation without effecting the basic composition.

The shaving liquid disclosed above has excellent stability properties with allantoin remaining in solution without crystallizing out over extended periods of time.

Although but one embodiment of the invention has been shown and described, it will be apparent to those skilled in the art that various changes and modifications may be made therein without departing from the spirit of the invention or from the scope of the appended claims.

What is claimed is:

1. A stable soothing hydroalcoholic liquid shaving preparation comprising:
   a combined allantoin-boric acid hydrolyzed solution with allantoin in an amount of at least about 0.02% by weight and boric acid in an amount of at least about 2% by weight of the preparation and
   glycerine, menthol, ethyl alcohol and perfume,
   said glycerine comprising about 3% by weight, said menthol comprising about 0.01% by weight, said ethyl alcohol comprising about 70% by weight and said perfume comprising about 5% by weight of the preparation.

2. The liquid shaving preparation set forth in claim 1 wherein:
   said hydrolyzed solution comprises approximately 10% by weight of the preparation.

3. The liquid shaving preparation set forth in claim 1 wherein:
   the water to alcohol weight ratio in the preparation is approximately 2 to 7.

4. The liquid shaving preparation set forth in claim 1 wherein:
   the total water in the preparation comprising approximately 20 percent by weight of the total preparation.

5. The liquid shaving preparation set forth in claim 1 in further combination with:
   a truce amount of a coloring agent.

6. The liquid shaving preparation set forth in claim 1 wherein by weight:
   said allantoin comprises approximately 2 grams,
   said boric acid comprises approximately 20 grams,
   said glycerin comprises approximately 30 grams,
   said menthol comprises approximately 1 gram,
   said ethyl alcohol comprises approximately 700 grams, and
   said perfume comprise approximately 50 grams.

7. A method of manufacturing a stable soothing hydroalcoholic liquid shaving preapration comprising the steps of:
   mixing a first solution comprising perfume, menthol and ethyl alcohol,
   said first solution comprising approximately 50 grans of perfume, 1 gram of menthol and 500 cubic centimeters of 96% ethyl alcohol,
   mixing a second solution comprising heated distilled water having dissolved therein allantoin and boric acid,
   said second solution comprises approximately 118 cubic centimeters of distilled water having dissolved into it approximately 2 grams of allantoin and approximately 20 grams of boric acid at a distilled water temperature of 70 degrees Centigrade,
   cooling said second solution to approximately atmospheric temperature,
   adding and stirring into the cooled second solution 30 grams of glycerine to form a third solution,
   mixing approximately 2,450 cubic centimeters of distilled water with 1 gram of a coloring agent to form a fourth solution,
   adding said fourth solution to said third solution to form a fifth solution,
   adding approximately 230 cubic centimeters of ethyl alcohol to said fifth solution to form a sixth solution,
   adding said sixth solution to said first solution to form a seventh solution, adding one tablespoon of magnesium carbonate per liter of said second solution to said seventh solution to form an eighth solution, steeping said eighth solution from 15 days to 22 days at about 4 degrees Centigrade, filtering said eighth solution to form said preparation, and bottling said preparation.

8. The method of manufacture set forth in claim 7 wherein:

said coloring agent comprises Eosin.

9. The method of manufacture set forth in claim 7 in further combination with the step of adding a 50% solution of Trietholanolamine to cause the liquid shaving preparation to have a PH rating between 6.5 and 7.5.

10. The method of manufacture set forth in claim 7 in further combination with the step of reducing the ethyl alcohol and water sufficiently to compensate for the addition of 2% of a cetiol He material composition to aid in the treatment of dry skin.

* * * * *

UNITED STATES PATENT OFFICE
CERTIFICATE OF CORRECTION

Patent No. 4,963,350         Dated October 16, 1990

Inventor(s) Samuel A. Goldstein and Jose A. P. Alonso

It is certified that error appears in the above-identified patent and that said Letters Patent is hereby corrected as shown below:

Claim 5, line 3, cancel "truce" and substitute

---trace---.

Signed and Sealed this

Twenty-first Day of January, 1992

Attest:

HARRY F. MANBECK, JR.

Attesting Officer        Commissioner of Patents and Trademarks